United States Patent

Werner

[11] 4,000,287
[45] Dec. 28, 1976

[54] ISOINDOLINOPIPERIDINES

[75] Inventor: Lincoln Harvey Werner, Summit, N.J.

[73] Assignee: Ciba-Geigy Corporation, Ardsley, N.Y.

[22] Filed: Dec. 16, 1974

[21] Appl. No.: 533,107

[52] U.S. Cl. .......................... 424/267; 260/293.52; 260/293.61; 260/295 B

[51] Int. Cl.² ...................................... C07D 401/04

[58] Field of Search ............. 260/293.61; 424/267

[56] References Cited

UNITED STATES PATENTS

| 3,705,162 | 12/1972 | Graudums et al. | 260/281 |
| 3,956,335 | 5/1976 | Wilhelm et al. | 260/293.7 |

Primary Examiner—G. Thomas Todd
Attorney, Agent, or Firm—Joseph G. Kolodny; Theodore O. Groeger; John J. Maitner

[57] ABSTRACT

1-(3-Aryloxy-2-hydroxypropyl)-3- or 4-(1-oxoisoindolino)-piperidines, e.g. those of the formula

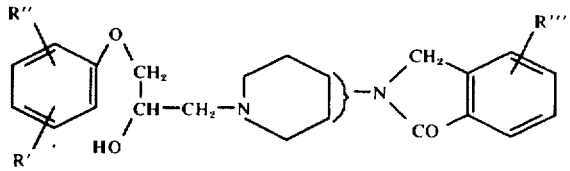

R' = alk (en, in) yl, cycloalkyl, OH, alk (en, in) yloxy, halo, $CF_3$ or CN
R'',R''' = H, alkyl, OH, alkoxy, halo, $CF_3$, $NO_2$, $NH_2$ or alkanoylamino 2-alkanoic acid esters and acid addition salts thereof are antihypertensive and antiarrhythmic agents.

8 Claims, No Drawings

ISOINDOLINOPIPERIDINES

SUMMARY OF THE INVENTION

The present invention concerns and has for its object the provision of new 1-(3-aryloxy-2-hydroxypropyl)-3- or 4-(1-oxoisoindolino)-piperidines, their esters and salts, more particularly of those corresponding to Formula I

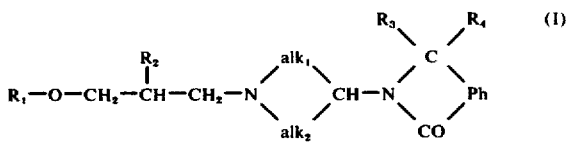

wherein $R_1$ is an optionally substituted aryl radical, $alk_1$ and $alk_2$ independently of one another are lower alkylene separating the adjacent nitrogen atom and methine group of either 2 carbon atoms, or $alk_1$ is lower alkylidene and $alk_2$ is lower alkylene separating said adjacent moieties by 3 carbon atoms, $R_2$ is an optionally acylated hydroxy group, $R_3$ is hydrogen or lower alkyl, $R_4$ is hydrogen or $R_4$ together with $R_3$ represent oxo, and Ph is an optionally substituted o-phenylene radical, or of salts thereof, as well as of pharmaceutical preparations in which said compounds or salts are present, and of processes for the manufacture and application of these products, which are useful antihypertensive, vasodilating, antiarrhythmic, noradrenolytic and positively inotropic agents.

DESCRIPTION OF THE PREFERRED EMBODIMENTS

An optionally substituted aryl radical $R_1$ is, for example, phenyl, indenyl or napththyl substituted by one, two or more substituents and also, for example, optionaly substituted 2,3-dihydro-5- or -6-indenyl or 5,6,7,8-tetrahydro-1- or -2-naphthyl. A monosubstituted or disubstituted phenyl or naphthyl radical is preferred, and a monosubstituted phenyl radical is preferred very particularly.

The aryl radical $R_1$ is, for example, substituted by aliphatic or cycloaliphatic hydrocarbon radicals, especially by lower aliphatic hydrocarbon radicals which an also be substituted. Examples of such optionally substituted lower aliphatic and cycloaliphatic hydrocarbon radicals are lower alkyl, lower alkenyl or lower alkinyl groups; 5 to 7 ring-membered cycloalkyl groups; lower alkoxy-lower alkyl, lower alkylthio-lower alkyl, hydroxy-lower alkyl, halogeno-lower alkyl, carbamoyl-lower alkyl, lower alkoxy-carbonylamino-lower alkyl and acylamino-ethenyl groups.

A substituent of an aryl radical $R_1$ can also be hydroxy which is optionally etherified by an aliphatic hydrocarbon radical, especially by a lower aliphatic hydrocarbon radical, which can be substituted yet further. Examples of such are lower alkoxy, lower alkenyloxy, lower alkinyloxy, hydroxy-lower alkoxy, lower alkoxy-lower alkoxy, lower alkylthio-lower alkoxy and aryl-lower alkoxy, such as phenyl-lower alkoxy groups.

The aryl radical $R_1$ can be also be substituted by the following substituents: halogen atoms or lower alkanoyl, lower alkanoyloxy, lower alkylmercapto, acylamino, nitrile, amino and nitro groups; optionally substituted carbamoyl, such as, N-mono-lower alkylcarbamoyl, N,N-di-lower alkylcarbamoyl or N,N-lower alkylenecarbamoyl groups; as well as optionally substituted ureido groups.

Substituents of the aryl radical which should be singled out particularly are, for example, optionally lower-alkylated carbamoyl, carbamoylalkyl, acylaminoethenyl, such as lower alkanoylaminoethenyl and lower alkoxycarbonylamino-lower alkyl radicals (which are preferably in the para-position on the phenyl radical), as well as nitrile groups (which are preferably in the ortho-position on the phenyl radical) and lower alkanoyl radicals (which are preferably in the ortho- or para-position on the phenyl radical). However, particularly preferred substituents on the aryl radical are halogen atoms (which are preferably in the ortho or para-position on the phenyl radical), and hydroxy, and above all lower alkoxy-lower alkyl and acylamino groups (which are preferably in the para-position on the phenyl radical), as well as lower alkyl, lower alkenyl, 5 to 7 ring-membered cycloalkyl, lower alkoxy, lower alkenyloxy and lower alkinyloxy groups (which are preferably in the ortho-position on the phenyl radical).

Examples of lower alkylene radicals $alk_1$ and $alk_2$ are 2,3-butylene, 1,2-butylene, or preferably 1,2-propylene, or especially 1,2-ethylene radicals; but $alk_1$ is also a methylidene or ethylidene and $alk_2$ a 1,3-propylene radical.

The o-phenylene radical Ph can carry one, two or more substituents; however, it preferably does not contain more than two substituents selected in particular from lower alkyl, lower alkoxy, halogeno, trifluoromethyl and hydroxy and, as a second choice, also from acylamino, nitro and amino.

An optionally acylated hydroxy group $R_2$ is, for example, lower alkanoyloxy, such as acetoxy, propionyloxy, butyryloxy or preferably pivaloyloxy, but above all the free hydroxy group.

Where not stated otherwise, lower radicals are those containing not more than 7 carbon atoms and preferably up to 4 carbon atoms.

Examples of lower alkyl groups are methyl, ethyl, n-propyl or isopropyl, straight-chain or branched butyl, pentyl or hexyl, which can be bonded in any position.

Lower alkenyl groups are, in particular allyl or methallyl, and a possible lower alkinyl group is above all propargyl.

Of the 5 to 7 ring-membered cycloalkyl groups cyclohexyl is preferred.

Lower alkoxy-lower alkyl radicals are, for example, those composed of the lower alkyl groups mentioned, for example, methoxymethyl, ethoxymethyl, n-propoxymethyl, n-butoxymethyl, 2-(n-butoxy)-ethyl, 3-(n-propoxy)-n-propyl or especially 2-methoxyethyl.

Lower alkylthio-lower alkyl radicals are, for example, those composed of the lower alkyl groups mentioned and are thus, for example, methylthiomethyl, 2-ethyltioethyl, 3-methyltio-n-propyl and especially 2-methylthioethyl.

Hydroxy-lower alkyl groups are above all those in which the lower alkyl part has the above meaning, such as, for example, 2-hydroxyethyl, 3-hydroxy-n-propyl and especially hydroxymethyl.

Possible halogeno-lower alkyl radicals are especially those which are derived from the alkyl groups mentioned and in which the halogen atom is a bromine or especially a chlorine or fluorine atom, such as, chloromethyl, 2-chloroethyl, dichloromethyl and especially trifluoromethyl.

Lower alkoxycarbonylamino-lower alkyl and carbamoyl-lower alkyl radicals are, for example, those wherein the lower alkyl parts are derived from the lower alkyl groups mentioned and carbamoyl is N-unsubstituted, such as methoxycarbonylaminomethyl, ethoxycarbonylaminomethyl, 4-methoxycarbonylamino-n-butyl, 2-ethoxycarbonylaminoethyl, 3-ethoxycarbonylamino-n-propyl and especially 2-methoxycarbonylamino-ethyl and 3-metoxy-carbonylamono-n-propyl; carbamoylmethyl or 2-carbamoyl-ethyl.

Acylamino-ethenyl groups are in particular radicals of the formula

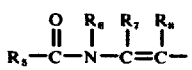

wherein $R_5$ is lower alkyl, lower alkoxy primary, secondary or tertiary amino, preferably mono- or di-lower alkylamino, each of $R_6$ and $R_8$ is hydrogen or a lower alkyl and $R_7$ is hydrogen, lower alkyl, carboxy or lower alkoxycarbonyl, wherein all of said lower alkyl or lower alkoxy parts in said formula are, for example, one of those mentioned above or below.

Lower alkoxy radicals are especially those derived from the lower alkyl groups mentioned, such as methoxy, ethoxy, n-propoxy, isopropoxy, n-butoxy and n-amyloxy. Two lower alkoxy radicals, especially two adjacent lower alkoxy radicals, can also be linked, as in the case of lower alkylenedioxy, for example, methylenedioxy.

Examples of lower alkenyloxy radicals are allyloxy or methallyloxy and a lower alkinyloxy radical is in particular propargyloxy.

Hydroxy-lower alkoxy radicals are especially those derived from the hydroxy-lower alkyl groups mentioned, but wherein preferably the two oxygen atoms are separated by at least 2 carbon atoms.

Lower alkoxy-lower alkoxy radicals are, for example, those derived from the lower alkoxy radicals mentioned, such as methoxymethoxy, ethoxymethoxy, 1-methoxyethoxy, 4-methoxy-n-butoxy, 3-methoxy-n-butoxy and especially 3-methoxy-n-propoxy, 2-methoxyethoxy and 2-ethoxyethoxy.

Lower alkylthio-lower alkoxy radicals are, for example, those groups which are derived from the lower alkyl groups mentioned, such as, methylthiomethoxy, 2-ethyltioethoxy, 3-methylthio-n-propoxy and especially 2-methylthioethoxy.

Phenyl-lower alkoxy radicals are especially α-phenyl-lower alkoxy radicals, such as benzyloxy, but can also be derived from the other lower alkyl groups mentioned, such as phenethoxy.

Lower alkanoyl radicals to be mentioned are preferably pivaloyl, propionyl or butyryl, but above all acetyl. Examples of alkanoyloxy radicals are those in which the alkanoyl part has the above meaning.

Lower akylmercapto groups are those derived from the lower alkyl groups mentioned, such as ethylmercapto, isopropylmercapto, n-butylmercapto and especially methylmercapto.

Acylamino groups are especially those which contain cycloaliphatic, aromatic, araliphatic and above all aliphatic acyl moieties corresponding to the formula R-CO-, wherein R is especially lower alkyl, for example one of those mentioned.

Cycloaliphatic acyl radicals of the formula R°-CO- are especially those in which R° denotes an optionally lower alkylated lower cycloalkyl radical, above all with 3–7, especially 5–7 ring members, such as cyclopropyl, cyclopentyl, cyclohexyl or cycloheptyl.

Aromatic or araliphatic acyl radicals are, for example, benzoyl and naphthoyl radicals, and phenyl-lower alkanoyl radicals are, for example, phenylacetyl and α- and - β -phenylpropionyl radicals.

Said acyl radicals can be mono-, di or polysubstituted, especially the aromatic and araliphatic acyl radicals, wherein the substituents preferably being present in the rings are selected from lower alkyl, lower alkoxy, halogen or trifluoromethyl, such as those mentioned above or below.

Preferred acyl radicals are benzoyl and particularly lower alkanoyl, such as acetyl.

Possible halogen atoms are especially fluorine or bromine but particularly chlorine.

The N-mono-lower alkylcarbamoyl and N,N-di-lower alkylcarbamoyl groups for example contain, as the lower alkyl part, the above mentioned lower alkyl groups and the N,N-lower alkylenecarbamoyl radicals contain, as lower alkylene radicals, especially 1,4-butylene or 1,5-pentylene. Examples of such radicals are N-methylcarbamoyl, N,N-dimethylcarbamoyl, pyrrolidino-carbonyl and piperidino-carbonyl.

An optionally substituted ureido group is, for example, such substituted by lower alkyl, for example, those mentioned above, such as, N',N'-dimethylureido or N',N'-diethylureido. It can also be substituted by divalent radicals, which can be optionally interrupted by hetero-atoms and/or substituted. Such radicals are preferably lower alkylene groups, which can be straight-chain or branched and above all have 4–6 chain carbon atoms if the carbon chain is uninterrupted, or 4 or 5 carbon atoms if the carbon chain is interrupted by hetero-atoms. Possible hetero-atoms are, in particular, oxygen, sulphur and nitrogen. Examples of such radicals are 1,4-butylene, 1,5-pentylene, 1,5-hexylene, 2,5-hexylene, 1,6-hexylene, 1,6-heptylene, 3-oxapentylene-(1,5), 3-oxahexylene-(1,6), 3-thia-pentylene-(1,5), 2,4-dimethyl-3-thia-pentylene-(1,5) and 3-lower alkyl-3-aza-pentylene-(1,5), such as 3-methyl-3-aza-pentylene-(1,5) or 3-aza-hexylene-(1,6).

The new compounds possess valuable pharmacological properties. Thus they show a blood pressure-lowering action, as can be demonstrated in animal experiments, for example on intravenous administration of doses of about 0.01–1 mg/kg to narcotised cats. Furthermore, the new compounds cause an inhibition of tachycardia, as can also be shown in animal experiments, for example in vitro experiments at concentrations of 0.3–3 γ/ml on an isolated guineapig heart by the Langendorff method (resolution of the tachycardia by isoproterenol [5 × 10⁻⁹ γ/ml] or histamine [3 × 10⁻⁷ γ/ml]). Furthermore, the new compounds cause a vasodilatation which can be demonstrated on animals, for example on narcotised dogs, by measuring the haemodynamics after intraduodenal administration of a dose of about 10 mg/kg.

The new compounds further possess a noradrenolytic action which can be demonstrated in vitro, for example in experiments on isolated perfused mesenteric arteries of rats at concentrations of 0.001–0.01 γ/ml.

The new compounds further show an anti-arrythmic and positively inotropic effect.

Accordingly, they are particular useful as antihypertensive and vasodilating agents. Furthermore, the new compounds can serve as starting materials or intermediate products for the manufacture of other compounds, especially pharmaceutically active agents.

Compounds to be mentioned particularly are those of Formula II

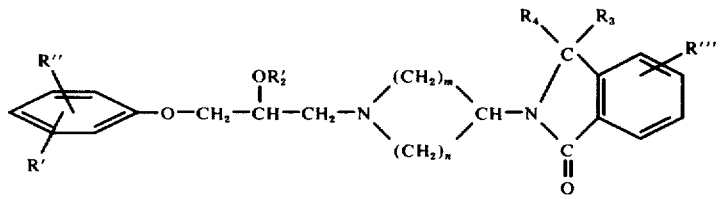

wherein m is 1 or 2, n is 2 or 3 and (m + n) is 4, R' is hydrogen, lower alkyl, lower alkenyl, lower alkinyl, 5 to 7 ring-membered cycloalkyl, carbamoyl-lower alkyl, hydroxy, lower alkoxy, lower alkenyloxy, lower alkinyloxy, halogeno, trifluoromethyl or cyano, each of R'' and R''' is hydrogen, lower alkyl, hydroxy, lower alkoxy, halogeno, trifluoromethyl, nitro, amino or lower alkanoylamino, $R_2'$ is hydrogen or lower alkanoyl, particularly acetyl, propionyl or pivaloyl, each of $R_3$ and $R_4$ denote a hydrogen atom, or $R_3$ together with $R_4$ represents oxo, and their therapeutically useful acid addition salts. In said compounds R' preferably is in one of the ortho-positions, R'' is one of the meta-positions or the para-position and R''' is preferably meta to carbonyl and para to methylene.

Compounds to be mentioned especially are in particular those of Formula II, wherein m is 1 or 2, n is 2 or 3 and (m + n) is 4, R' is methyl, allyl, cyclohexyl, carbamoylmethyl, methoxy, allyloxy, propargyloxy, chloro, bromo, trifluoromethyl or cyano, R''' is hydrogen, methyl, methoxy or acetylamino, $R_2'$ is hydrogen, acetyl, propionyl or pivaloyl, and each of $R_3$ and $R_4$ is hydrogen, and salts thereof. Of said compounds with m = 1 or 2, n = 2 or 3 and (m + n)=4, R' is preferably o-methyl, o-allyl, o-cyclohexyl, p-carbamoylmethyl, o-methoxy, o-allyloxy, o-propargyloxy, o- or p-chloro, -bromo or -trifluoroemthyl or o-cyano, R'' is preferably hydrogen, m-methyl, m-methoxy or m-acetylamino, $R_2'$ is hydrogen, acetyl, propionyl or pivaloyl, and each of R''', $R_3$ and $R_4$ is hydrogen, and their therapeutically useful acid addition salts.

Compounds to be mentioned specifically are 1-[3-(o-methoxy-phenoxy)-2-hydroxypropyl]-4-(1-oxo-isoindolino)-piperidine and the 1-[3-(o-cyanophenoxy)-2-hydroxypropyl]-4-(1-oxo-isoindolino)-piperidine and their therapeutically useful acid addition salts, which, for example, when administered intravenously, in a dose of about 0.01 mg/kg, to narcotised cats, cause a distinct lowering of the blood pressure.

The new compounds are obtained according to methods which are in themselves known, for example, by reacting compounds of the formulae

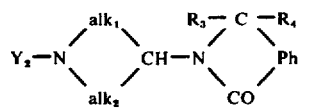

wherein $R_1$, $alk_1$, $alk_2$, Ph, $R_3$ and $R_4$, have the indicated meanings, one of the radicals $Y_1$ and $Y_2$ represents hydrogen and the other denotes a radical of the formula $$-CH_2-CH-CH_2-Z$$
$$\phantom{-CH_2-C}|$$
$$\phantom{-CH_2-CH-CH_2-}X$$

and X represents the group $R_2$, wherein $R_2$ has the indicated meaning, and Z denotes a reactively esterified hydroxy group, or X and Z together form an epoxy group.

Thus, for example, a possible procedure is to react a compound of the formula $$R_1-O-CH_2-\underset{\underset{X}{|}}{CH}-CH_2-Z \qquad (IIIc)$$

with a compound of the formula

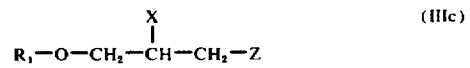

wherein $alk_1$, $alk_2$, Ph, $R_3$ and $R_4$ have the above meanings and either X represents the group $R_2$, wherein $R_2$ has the indicated meanings, and Z represents a reactive esterified hydroxy group, or X and Z together form an epoxy group.

A reactive esterified hydroxy group is, in particular, such esterified by a strong inorganic or organic acid, above all a hydrohalic acid, such as hydrochloric, hydrobromic or hydriodic acid; sulphuric acid; or an organic sulphonic acid, for example benzenesulphonic, p-bromobenzenesulphonic or p-toluenesulphonic acid. Thus, Z in particular represents chlorine, bromine or iodine.

This reaction is carried out in the usual manner. When a reactive ester is used as the starting material, the above reaction is preferably carried out in the presence of a basic condensation agent and/or with an excess of the compound of the formula IIId.

Further, a compound of the formula $R_1$ - OH (IIIe) wherein $R_1$ has the above meanings, can be reacted with a compound of the formula

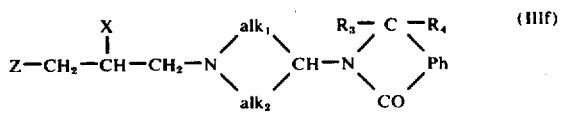

wherein X, Z $alk_1$, $alk_2$, Ph, $R_3$ and $R_4$ have the above meanings.

This reaction is carried out in the usual manner. If reactive esters are used as the starting material, the compound of Formula IIIe can be used in the form of its metal phenolate, such as alkali metal, e.g. sodium phenolate, or the reaction is carried out in the presence of an acid-binding agent, especially of a condensation agent, which can form a salt with the compound of the Formula IIIe, such as an alkali metal alcoholate.

The new compounds in which $R_3$ is hydroxy can furthermore be manufactured by reducing the oxo group of the propyl chain to a hydroxy group in a compound of the formula

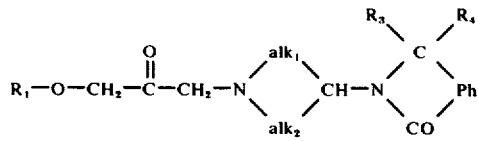

wherein $R_1$, $alk_1$, $alk_2$, Ph, $R_3$ and $R_4$ have the above meanings

This reduction is carried out in the usual manner, in particular using a di-light metal hydride, such as sodium borohydride. However, the reduction can also be carried out with nascent hydrogen, which can be obtained by reaction of metals or metal alloys on agents which provide hydrogen, such as carboxylic acids, alcohols or water, in particular zinc or zinc alloys together with acetic acid, or alkali metals and alcohols, such as sodium and ethanol.

The reduction can furthermore be carried out by catalytic hydrogenation, such as with hydrogen in the presence of a hydrogenation catalyst, for example heavy metals such as palladium, platinum or Raney nickel. Care must be taken that other reducible groups are not attacked during the reduction.

The new compounds can also be obtained when the pyridinium ring is reduced to the piperidine ring in a compound of the formula

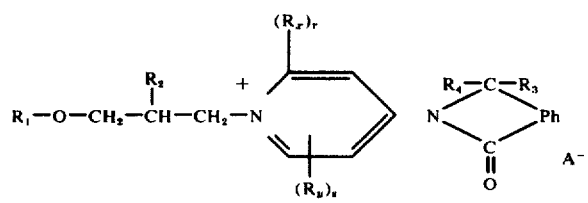

wherein $R_1$, $R_2$, $R_3$ and $R_4$ have the above meanings, $R_x$ and $R_y$ independently of one another denote lower alkyl radicals or hydrogen atoms and r, s represent 1 or 2, and $A^-$ is an anion.

The reduction can be carried out in the usual manner, preferably by catalytic hydrogenation, such as with hydrogen in the presence of a hydrogenation catalyst, for example heavy metals, such as pallium, platinum or Raney nickel, or with nascent hydrogen, such as, for example, is produced by sodium and an alcohol, such as lower alkanol, for example ethanol. Care must be taken that other reducible groups are not attacked in the reduction.

The new compounds can also be obtained by intramolecular condensation of a compound of the formula

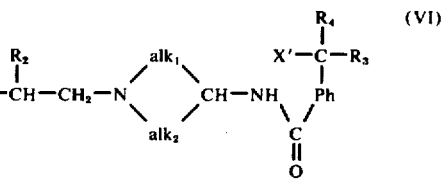

wherein $R_1$, $R_2$, $alk_1$, $alk_2$, Ph, $R_3$ and $R_4$ have the indicated meanings and X' denotes a reactive esterified hydroxy group, in particular one of those mentioned above.

The cyclisation (intramolecular condensation) can be carried out in the usual manner, preferably in the presence of a solvent, such as an inert polar solvent, for example an alcohol, e.g. ethanol or isopropanol; or dimethylformamide, and advantageously in the presence of a condensation agent, particularly of a basic condensation agent, preferably in the presence of an alkali metal hydroxide, carbonate or bicarbonate, or alkaline earth metal hydroxide, carbonate or bicarbonate, for example sodium hydroxide, potassium hydroxide, calcium hydroxide, sodium carbonate, potassium carbonate, calcium carbonate, sodium bicarbonate or potassium bicarbonate, or of an alkali metal acetate, such as sodium acetate, or of an alkali metal alcoholate, such as sodium methylate, or of organic tertiary nitrogen bases, such as trialkylamines, for example trimethylamine or triethylamine; or pyridine.

The new compounds can also be obtained by intramolecular condensation of a compound of the formula (VII)

$$R_1-O-CH_2-\overset{R_2}{\underset{|}{CH}}-CH_2-N\begin{Bmatrix}alk_1\\ \\alk_2\end{Bmatrix}CH-N\begin{Bmatrix}\overset{R_4}{\underset{|}{C}}-R_3\\Ph\\Y_3\\H\end{Bmatrix}$$

wherein $R_1$, $R_2$, $alk_1$, $alk_2$, $R_3$ and $R_4$ and Ph have the indicated meanings, and $Y_3$ denotes a free or preferably functionally modified carboxy group which contains oxo.

A functionally modified carboxy group which contains oxo is, for example, an esterified carboxy group, in particular, a carboxy group esterified with a lower alkanol or aralkanol, such as methanol, phenol, p-nitrophenol or benzyl alcohol, or an activated esterified carboxy group, such as esterified with cyanomethanol, or an acid halide group, in particular, the acid chloride group or an acid azide, amide or anhydride grouping. Possible acid anhydride groupings are especially those of mixed anhydrides, especially of mixed anhydrides with carbonic acid monoalkyl esters, such as carbonic acid monoethyl ester or carbonic acid monisobutyl ester.

The reaction can be carried out in the usual manner, preferably elevated temperatures are used. The reaction is advantageously carried out in a solvent, such as an inert solvent, for example a hydrocarbon, such as benzene or toluene, or in a high-boiling inert solvent such as, for example, diphenyl ether.

The new compounds in which $R_2''$ represents hydrogen, can also be obtained when, in a compound of the formula

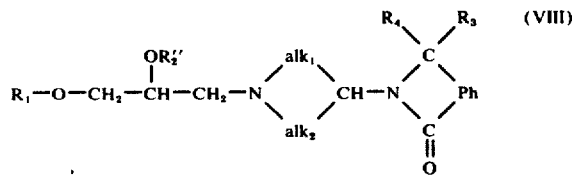

wherein $R_1$, $alk_1$, $alk_2$, Ph, $R_3$ and $R_4$ have the indicated meanings and $R_2''$ denotes a radical which can be split off by hydrogenolysis, $R_2''$ is split off by hydrogenolysis.

A radical which can be split off by hydrogenolysis is above all an α-aralyl radical, such as benzyl, or an α-aralkoxycarbonyl radical, such as carbobenzoxy. The hydrogenolysis can be carried out in the usual manner, preferably by means of hydrogen in the presence of a hydrogenation catalyst, such as a nickel, palladium, platinum or ruthenium catalyst.

The new compounds of the Formula I, wherein $R_4$ together with $R_5$ forms an oxo group, can also be obtained when a compound of the formula

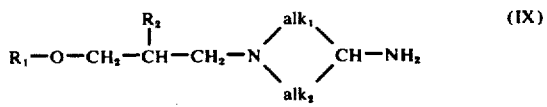

wherein $R_1$, $R_2$, $alk_1$ and $alk_2$ have the above meanings, is reacted with a compound of the formula

wherein $R_3$, $R_4$ and Ph have the above meanings and $Y_3$ and $Y_3'$ independently of one another represent a free carboxy group or preferably a functionally modified carboxy group which contains oxo, or together represent the anhydride grouping —CO—O—CO—.

A functionally modified carboxy group which contains oxo is, for example, an esterified carboxy group such as, in particular, a carboxy group esterified with a lower alkanol or aralkanol, such as methanol, phenol, p-nitrophenyl or benzyl alcohol, or an activated esterified carboxy group, such as a carboxy group esterified with cyanomethanol, or an acid halide group, in particular, the acid chloride group, or an acid azide, amide or anhyride grouping. Possible acid anhydride groupings are in particular those of mixed anhydrides, especially of mixed anhydrides with carbonic acid monoalkyl esters, such as carbonic acid monoethyl ester or carbonic acid monoisobutyl ester.

The reaction can be carried out in the usual manner. Preferably, elevated temperatures are used. The reaction is advantageously carried out in a solvent, such as an inert solvent, for example a hydrocarbon, such as benzene or toluene, or in a high-boiling inert solvent such as, for example, diphenyl ether.

The new compounds of the Formula I can also be obtained when a compound of the formula

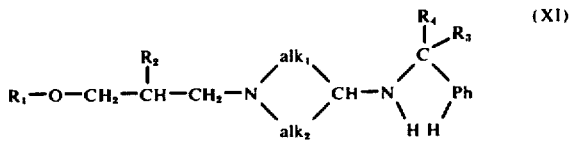

wherein $R_1$, $R_3$, $R_4$, $alk_1$, $alk_2$ and Ph have the above meanings and $R_2$ preferably denotes an acylated hydroxy group, is reacted with carbonic acid or one of its reactive derivatives.

Examples of reactive carbonic acid derivatives are carbonyl halides, such as, in particular, phosgene, and also carbonic acid monoesters or diesters such as, for example, carbonic acid mono- or di-lower alkyl esters, such as carbonic acid monomethyl or monoethyl ester, carbonic acid di-methyl or diethyl ester and also, for example, halogenoformic acid esters, for example, halogenoformic acid lower alkyl esters, such as chloroformic acid methyl or ethyl ester.

The reaction is carried out in the usual manner, preferably in the presence of a catalyst, such as a Lewis acid, such as a halide of zinc, cadminum or above all boron or aluminum, for example zinc chloride, aluminum chloride or bromide or boron trifluoride, optionally in the form of a complex, for example in the form of an etherate, and preferably in an inert solvent, such as an ether, for example in diethyl ether, tetrahydrofurane or dioxane, or in a chloroalkane, for example in carbon tetrachloride, in an alkane, for example in a high-boiline petroleum fraction, or in carbon disulphide, preferably at normal or optionally moderately elevated temperature.

In resulting compounds, substituents can be split off, introduced or converted, within the scope of the end products.

Thus, for example, in compounds of Formula I, wherein $R_1$ denotes an aryl radical which is substituted by a radical $Z''$ which can be converted into an optionally substituted carbamoyl group, $Z''$ can be converted into an optionally substituted carbamoyl group.

A radical $Z''$ is in this case above all an optionally functionally modified carboxyl group containing an oxo group.

A functionally modified carboxy group which contains oxo is, for example, an esterified carboxy group, such as, in particular, carboxy esterified with a lower alkanol or aralkanol, such as methanol, phenol, p-nitrophenol or benzyl alcohol, or an activated esterified carboxy group, such as esterified with cyanomethanol, or an acid halide, in particular, the acid chloride grouping, or an acid azide or anhydride grouping. Possible acid anhydride groupings are in particular those of mixed anhydrides, especially of such with carbonic acid monoalkyl esters, such as carbonic acid monoethyl or monoisobutyl ester.

The conversion of the group $Z''$ is effected, for example, by reaction with ammonia or with a corresponding amine possessing at least 1 hydrogen atom.

The reaction is carried out in the usual manner, in particular at elevated temperature, if necessary at drastically elevated temperature, such as at a temperature which may even be above 200° C, if desired under pressure and if desired with an excess of the particular amine. If the reaction is carried out at room temperature or only moderately elevated temperature, it is preferably carried out in an inert solvent using a longer reaction time. Examples of inert solvents are alcohols, such as methanol and ethanol, ethers, such as diethyl ether or dioxane, benzene and the like.

Furthermore, for example, in compounds of the Formula I, wherein $R_1$ denotes an aryl radical substituted by a radical $Z'''$ which can be coverted into an optionally substituted ureido group, $Z'''$ can be coverted into said group.

$Z'''$ is in paticular a reactively modified carboxyamino radical, such as a carboxyamino esterified by a lower alkanol or phenol, or a corresponding halogencarbonylamino radical, in particular, a chlorocarbonylamino radical, or an isocyanato radical.

The conversion to the ureido group is carried out, for example, by reaction with ammonia or corresponding amine possessing at least 1 hydrogen atom. This reaction can be carried out in the usual manner, especially using an excess of ammonia or amine and optionally in a solvent and preferably at elevated temperature.

Furthermore, resulting compounds in which $R_1$ is an aryl radical substituted by hydroxyalkyl, hydroxyalkoxy, mercaptoalkyl or mercaptoalkoxy radical, can be alkylated, for example by reaction with a reactive ester of a corresponding alkanol. Reactive esters are here above all esters with strong inorganic or organic acids, preferably with hydrohalic acids, such as hydrochloric, hydrobromic or hydriodic acid; with sulphuric acid or with arylsulphonic acids, such as benzenesulphonic, p-bromobenzenesulphonic or p-toluenesulphonic acid.

The reaction can be carried out in the usual manner, advatageously in the presence of solvents and, for example, in the presence of condensation agents, such as basic condensation agents, at lowered, ordinary or elevated temperature.

Furthermore, in compounds of Formula I, wherein $R_1$ is an aryl radical substituted by a $Z_2$-alkyl or $Z_2$-alkoxy radical and $Z_2$ represents a reactively esterified hydroxy group, $R_1$ can be converted into alkoxy- or alkyl-mercapto-alkyl or -alkoxy radicals by reaction with alkanols or alkylmercaptans.

Reactively esterified hydroxyl groups are here in particular hydroxyl groups esterified with the strong acids mentioned. The reaction can be carried out in the usual manner, advantageously in the presence of solvents and, for example, in the presence of condensation agents, such as basic condensation agents, at lowered, ordinary or elevated temperature.

Furthermore, in compounds of Formula I wherein $R_1$ is an aryl radical substituted by hydroxy, the hydroxy group can be converted into a group of the formula $R_x$—O—, wherein $R_x$ denotes an alkyl, alkenyl, alkinyl, alkoxyalkyl or alkylmercaptoalkyl radical. This conversion can be effected in the usual manner, for example by reaction with a reactive ester of an alcohol of the formula $R_x$OH or a diazoalkane, such as diazomethane.

Reactive esters are above all esters with strong inorganic or organic acids, preferably with hydrohalic acids, such as hydrochloric, hydrobromic or hydriodic acid; with sulphuric acid or with arylsulphonic acids, such as benzenesulphonic, p-bromobenzenesulphonic or p-toluenesulphonic acid.

The reaction can be carried out in the usual manner, advantageously in the presence of solvents. When using the reactive esters, the reaction is preferably carried out in the presence of condensation agents, such as basic condensation agents, or the phenolic hydroxy compound is employed in the form of a salt, for example a metal salt, such as an alkali metal salt, for example the sodium or potassium salt. The reaction can be carried out at lowered, ordinary or elevated temperature.

Furthermore it is possible, in compounds of the Formula I, wherein $R_1$ denotes an aryl radical substituted by an amino group or by a substituent containing an amino group, and/or Ph denotes an o-phenylene radical containing an amino group, to acylate said amino group or groups, for example, by reaction with an acylating agent.

Possible acylating agents are carboxylic acids, for example aliphatic, araliphatic or cycloaliphatic carboxylic acids, preferably in the form of their functional derivatives, such as halides, especially chlorides, or anhydrides, for example pure or mixed anhydrides, or inner anhydrides, such as ketenes.

Furthermore, in compounds of Formula I which contain hydroxy groups, these groups can be acylated (esterified). The acylation is carried out in the usual manner, for example by reaction with carboxylic acids, advantageously in the form of their reactive functional derivatives, such as açid halides, for example chlorides, esters, especially esters with lower alkanols, such as methanol and ethanol, or activated esters such as cyanomethyl esters, or pure or mixed anhydrides, for example mixed anhydrides with carbonic acid monoalkyl esters such as carbonic acid monoethyl ester and monoisobutyl ester.

In compounds of Formula I which contain an acylated hydroxy or amino group, this group can be split in the usual manner to give the free hydroxy or amino group respectively, and can in particular be split hydrolytically, with appropriate acid or basic catalysts, for example with inorganic acids or alkali metal hydroxide solutions, for example, with hydrochloric acid or with aqueous sodium hydroxide solution. If such splitting should already occur in the course of one of the above methods of manufacture, a resulting free hydroxy or amino group can optionally be acylated as described above.

In compounds of Formula I which contain a halogen atom, for example chlorine or bromine, on an aromatic ring, for example on $R_1$ or Ph, this halogen atom can be replaced by hydrogen. This is done in the usual manner, for example by dehalogenating hydrogenation, such as hydrogenation in the presence of nickel or palladium catalysts. Compounds which contain an unsubstituted aryl radical or an aryl radical which is partly substituted by other groups, can be halogenated at the aryl radical. This can be done in the usual manner, for example with halogen, especially at non-elevated temperatures or with cooling, and in the presence of a catalyst, such as iron, iodine, iron-III chloride or aluminum chloride or the corresponding bromides.

In resulting compounds which contain an unsubstituted aryl radical $R_1$, this radical can be nitrated. The nitration is carried out in a manner which is in itself known, for example by treatment with a mixture of concentrated sulphuric acid and concentrated nitric acid or with the mixed anhydride or nitric acid and a carboxylic acid, for example a lower alkanecarboxylic acid, such as acetic acid.

Furthermore, in compounds of Formula I which contain substituents with a C-C double bond or C-C triple bond, said bonds can be converted into a C-C single bond by catalytic hydrogenation, such as by hydrogen in the presence of a hydrogenation catalyst, for example nickel, platinum or palladium, such as Raney nickel, platinum black or palladium on active charcoal. Care must be taken at the same time that other reducible groups are not attacked.

In compounds of Formula I, which contain substituents with a C-C triple bond, this bond can furthermore be reduced merely to a C-C double bond and can, if desired, be reduced stereospecifically to a C-C-cis- or C-C-trans-double bond. The reduction of a C-C triple bond to a C-C double bond can be carried out, for example, by hydrogenation with 1 mol of hydrogen in the presence of a less active hydrogenation catalyst, such as iron or palladium, for example Raney iron or palladium on barium sulphate, especially at elevated temperature. The reduction to a C-C-cis double bond can be effected, for example, by means of 1 mol of hydrogen in the presence of a deactivating catalyst, such as palladium on animal charcoal in the presence of quinoline, palladium on calcium carbonate in the presence of lead salts, or Raney nickel. The reduction to a C-C-trans-double bond can be effected, for example, by means of sodium in liquid ammonia, in which case, especially taking into account a urea group, short reaction times and no excess reducing agent are employed and, if appropriate, an ammonium halide, such as ammonium chloride, is added as the catalyst.

Furthermore it is possible, in resulting compounds of Formula I, wherein $R_2$, $R_3$, $R_4$, $alk_1$, $alk_2$ and Ph have the above meanings and $R_1$ is an aryl radical substituted by the group $Z_1$-lower alkyl, wherein $Z_1$ is a reactive esterified hydroxyl group, to convert this radical into an aryl radical substituted by a lower alkoxycarbonylamino-lower alkyl group, such as, for example by reaction with a carbamic acid lower alkyl ester of the formula: lower alkoxy-$CO$-$NH_2$.

In resulting compounds which contain a halogen atom, for example bromine or especially iodine, on an aromatic ring, this atom can be replaced by the trifluoromethyl group in the usual manner, for example by means of trifluoromethyl iodide in the presence of copper powder, especially in an aprotic solvent such as pyridine, dimethylformamide or acetonitrile.

In resulting compounds of FOrmula I which contain an α-aralkylamino or α-aralkoxycarbonylamino group or an α-aralkoxy or α-aralkoxycarbonyloxy group, these can be split to give free amino or hydroxy groups respectively. α-Aralkyl is in such cases especially benzyl. The splitting-off can be effected in the usual manner, especially by means of hydrogen in the presence of a hydrogenation catalyst, such as a palladium, platinum or nickel catalyst.

In resulting compounds of Formula I which possess nitro groups on an aromatic nucleus, these groups can be reduced to amino groups. The reduction can be carried out in the usual manner for example by nascent hydrogen (for example with iron and hydrochloric acid or with aluminum amalgam) or with catalytically activated hydrogen, such as hydrogen in the presence of platinum, nickel or palladium catalysts.

The reactions mentioned can optionally be carried out simultaneously or successively, and in optional sequence. They can be carried out in the usual manner in the presence or absence of solvents or diluents, acid or basic condensation agents and/or catalysts, at lowered, ordinary or elevated temperature and if appropriate in a closed vessel under elevated pressure and/or under an inert gas atmosphere.

Depending on the process conditions and starting materials, the end products are obtained in the free form or in the form of their acid addition salts, which are also encompassed by the invention. Thus, for example, basic, neutral or mixed salts and at times also hemihydrates, monohydrates, sesquihydrates or polyhydrates thereof, can be obtained. The acid addition salts of the new compounds can be converted into the free commpounds in a manner which is in itself known, for example by means of basic agents, such as alkalis or ion exchangers. On the other hand, the resulting free bases can form salts with organic or inorganic acids. Acids used for the preparation of acid addition salts are especially those which are suitable for forming therapeutically usable salts. As examples of such acids there may be mentioned: hydrohalic acids, for example hydrochloric acid, sulphuric acids, for example sulphuric acid, phosphoric acids, nitric acid, perchloric acid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid, fumaric acid, benzoic acid, p-amino-benzoic acid, anthranilic acid, p-hydroxybenzoic acid, salicylic acid or p-aminosalicylic acid, embonic acid, methanesulphonic acid, ethanesulphonic acid, hydroxyethanesulphonic acid, ethylenesulphonic acid; halogenobenzenesulphonic acid, toluenesulphonic acid, naphthalenesulphonic acid or sulphanilic acid; methionine, tryptophane, lysine or arginine.

These or other salts of the new compounds, such as, for example, the picrates, can also serve for the purification of the resulting free bases by converting the free bases into salts, isolating these and again liberating the bases from the salts. Because of the close relationsghips between the new compounds in the free form and in the form of their salts, the free compounds are, in the preceding and following text, where appropriate also to be understood as the corresponding salts, with regard to general sense and intended use.

The invention also relates to those embodiments of the process, according to which a compound obtainable as an intermediate product at any stage of the process is used as the starting material and the missing process steps are carried out, or the process is discontinued at any stage, or in which a starting material is formed under the reaction conditions or in which a reactant is present, if appropriate, in the form of an optical antipode and/or of a salt.

Thus, for example, the new piperidines can be obtained if a compound of Formula IX is reacted with a compound of the formula X'-($R_3$, $R_4$) C-Ph-$Y_3$ a product of Formula VI is produced an an intermediate and then reacts further, in accordance with the invention, to give a compound of Formula I. The reaction can be carried out in the usual manner, for example as described above for the intramolecular condensations.

The new compounds can, depending on the choice of the starting materials and procedures, be in the form of optical antipodes or racemates or, if they contain at least two asymmetrical carbon atoms, also in the form of racemate mixtures and/or pure geometrical isomers or mixtures thereof (isomer mixtures).

Resulting isomer mixtures can be separated into the two pure geometrical isomers on the basis of the physicochemical differences of the constituents in a known manner, for example by chromatography on a suitable stationary phase, such as silica gel, or aluminum oxide, which has been pretreated with a complex-forming heavy metal compound, for example with a silver compound, or by forming a heavy metal addition compound, for example the silver nitrate complex, separating this into the addition compounds of the pure isomers, for example by fractional crystallisation, and subsequently liberating the pure isomers.

Resulting pure isomers, for example trans-isomers, can be converted in the usual manner, for example photochemically, for example by irradiation with light of a suitable wavelength, advantageously in a suitable solvent, such as aliphatic hydrocarbon, or in the presence of a suitable catalyst, into the isomers of opposite configuration, for example into the cis-isomers.

Racemate mixtures can be separated into the two stereo-isomeric (diastereomeric) pure racemates on the basis of the physico-chemical differences of the constituents in a known manner, for example by chromatography and/or fractional crystallisation.

Resulting racemates can be resolved according to known methods, for example by recrystallisation from an optically active solvent, with the aid of micro-organisms or by reaction with an optically active acid which forms salts with the racemic compound and separation of the salts obtained in this manner, for example on the basis of their different solubilities, into the disastereomers, from which the antipodes can be liberated by treatment with suitable agents. Particularly customary optically active acids are, for example, the D- and L-forms of tartaric acid, dio-toluyltartaric acid, malic acid, mandelic acid, camphorsulphonic acid or quinic acid. Advantageously, the more active L-antipode is isolated.

Suitably, those starting materials are used for carrying out the reactions according to the invention which lead to the initially particularly mentioned groups of end products and particularly to the end products which have been specifically described or singled out.

The starting materials are known or can, if they are new, be obtained according to methods which are in themselves known.

The compoudns of Formula IIId, used as preferred starting materials, can be obtained, for example, if a compound of the formula

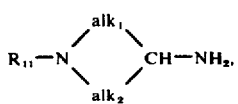

wherein alk$_1$ and alk$_2$ have the indicated meanings and R$_{11}$ denotes an α-aralkyl radical, such as a benzyl radical, is reacted with a compound of the formula

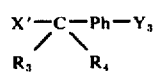

wherein R$_3$ and R$_4$ have the indicated meanings and X' and Y$_3$ have the meanings indicated for Formulae VI and VII, and in the resulting compound of the formula

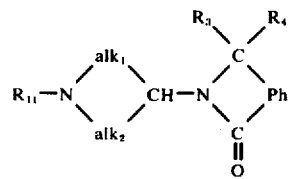

the α-aralkyl radical R$_{11}$ is replaced by hydrogen, for example by catalytic hydrogenation as described above.

The new compounds can be used as medicaments, for example in the form of pharmaceutical preparations in which they or their salts are present in a mixture with a pharmaceutical, organic or inorganic, solid or liquid excipient which is suitable, for example, for enteral, for example oral, or parenteral administration. Suitable materials for forming the excipient are those which do not react with the new compounds such as, for example, water, gelatin, lactose, starch, magnesium stearate, talc, vegetable oils, benzyl alcohols, gum, polyalkylene glycols, white petroleum jelly, cholesterol or other known medicinal excipients. The pharmaceutical preparations can be, for example, in the form of the usual tablets, dragees, capsules or suppositories, or in a liquid form, as solutions (for example as an elixir or syrup), suspensions or emulsions. They are optionally sterilised and/or contain auxiliaries, such as preservatives, stabilisers, wetting agents or emulsifiers, salts for regulating the osmotic pressure or buffers. They can also contain yet other therapeutically valuable materials. The preparations, which can also be used in veterinary medicine, are formulated according to customary methods.

The dosage of the new compounds depends on the nature of the conditions to be treated and on the individual requirements. For example, the new compounds can be administered to a warm-blooded animal of about 75 kg body weight in a daily dose of about 5–100 mg, especially about 5 to 60 mg.

The new compounds can also be used advantageously in pharmaceutical preparations in combination with other antihypertensive agents and/or diuretics.

Compounds, having an anti-hypertensive action, which can be used are in particular those of the type of α-amino-β-hydroxyphenyl-propionic acid and β-amino-β-alkoxyphenylpropionic acid and especially of the hydrazinopyridazines and of the sympathicolytics.

Suitable diuretics are materials which increase the diuresis both through renal and through extrarenal action on the tissues. For this purpose, substances with an inhibiting action on the back-resorption in the tubulus, such as, for example, in particular saluretics as well as ethacrinic acid and its analogues, can be used.

Particularly suitable compounds are benzothiadiazine derivatives, such as thiazides and hydrothiazides, benzenesulphonamides, phenoxyacetic acids, benzofurane-2-carboxylic acids and benzofurane-2,3-dihydroxy-2-carboxylic acids.

The examples which follow illustrate the invention without however restricting it. Temperatures are given in degrees Centrigrade and all parts wherever given are parts by weight. If not mentioned otherwise, all evaporations are performed under reduced pressure, e.g. between about 15 and 100 mm Hg.

EXAMPLE 1

The mixture of 3.8g of 1-(o-methoxyphenoxy)-2,3-epoxy-propane, 4.32 g of 4-(1-oxoisoindolino)-piperidine and 35 ml of isopropanol is refluxed for 4 hours while stirring. After cooling to room temperature it is acidified with saturated hydrogen chloride in ethyl acetate to reach the pH=1, and more cooled with an ice bath. It is filtered, the residue washed with ice-cold isopropanol and diethyl ether and recrystallized from 100 ml of isopropanol, to yield the 1-[3-(o-methoxyphenoxy)-2-hydroxypropyl]-4-(1-oxo-isoindolino)-piperidine hydrochloride of the formula

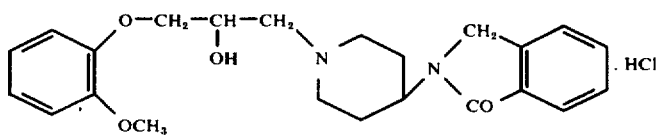

melting at 172°–174°.

The starting material is prepared as follows: The mixture of 150 g of 2-formylbenzoic acid, 85.2 g of 4-aminopyridine and 2.8 lt of toluene is refluxed on a water-separator for 2.5 hours while stirring and stirring is continued at room temperature over night. It is filtered and the residue washed with toluene, to yield the 1-(4-pyridylamino)-3-oxophthalan melting at 215°–220°. [Analogously the 1-(3-pyridylamino)-3-oxophthalan is obtained from 3-aminopyridine; m.p. 150°–155°].

To the suspension of 278 g thereof in 4.7 lt of anhydrous ethanol, 96 g of sodium borohydride are added portionwise during 105 minutes while stirring at 18°. Stirring is continued at room temperature over night, the mixture is filtered, the filtrate concentrated to a volume of 1.2 lt, cooled and the precipitate formed collected, to yield the 2-(4-pyridylaminometyl)-benzoic acid melting above 250°.

180.6 g thereof are added to 1.4 lt of concentrated sulfuric acid during 40 minutes while stirring and allowing the temperature to rise to about 67°. The mixture is stirred for 1 hour at about 95°, cooled to 25°, and slowly poured onto 4 kg ice. The mixture is neutralized with about 4.5 lt of aqueous ammonia, the precipitate formed filtered off and taken up in 2.3 lt of isopropanol and 600 ml of chloroform. The mixture is refluxed for 30 minutes, filtered hot, the filtrate cooled and the precipitate formed collected, to yield the 4(1-osoisoindolino)-pyridine.

The mixture of 30 g thereof, 400 ml of glacial acetic acid and 30 g of 10% palladium on charcoal is hydrogenated at about 65° and 3 atm until the theoretical amount of hydrogen has been absorbed. It is cooled to room temperature, filtered and evaporated. The residue is taken up in 6 N aqueous sodium hydroxide, the mixture extracted with chloroform, the extract washed with saturated aqueous sodium chloride, dried and evaporated, to yield the 4(1-oxoisoindolino)-piperidine melting at 144°–146°.

EXAMPLE 2

The mixture of 2.30 g of 1-(o-cyanophenoxy)-2,3-epoxy-propane, 2.84 g of 3(1-oxoisoindolino)-piperidine and 30 ml of isopropanol is refluxed for 4 hours while stirring. After cooling to room temperature it is acidified with saturated hydrogen chloride in ethyl acetate to reach the pH=1. The precipitated oil is separated, dissolved in water, the mixture extracted first with ethyl acetate, then made basic with 6N aqueous sodium hydroxide and again extracted with chloroform. The combined extracts are washed with water, dried, filtered and evaporated. 3.1 g of the residue are dissolved in 20 ml of ethyl acetate and the solution added to that of 1.42 g of cyclohexylsulfamic acid in 15 ml of hot isopropanol. The mixture is concentrated, the precipitate collected and triturated with diethyl ether, to yield the 1-[3-(o-cyanophenoxy)-2-hydroxypropyl]-3-(1-oxoisoindolino)-piperidine cyclamate of the formula

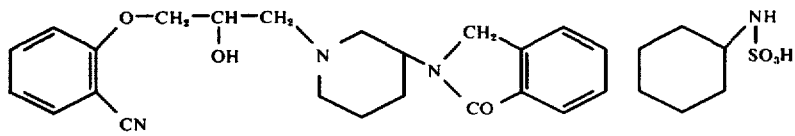

melting at 105°–115°.

The starting material is prepared as follows: To the suspension of 29 g of 1-(3-pyridylamino)-3-oxophthalan in 300 ml of anhydrous ethanol, 12 g of sodium borohydride are added portionwise during 45 minutes while stirring at 35°. After standing over night at room temperature the mixture is evaporated, the residue taken up in 150 ml of glacial acetic acid and 75 ml of concentrated hydrochloric acid, the mixture refluxed for 24 hours and evaporated. The residue is taken up in water, the mixture made basic with 6 N aqueous sodium hydroxide, filtered, the residue washed with water and recrystallized from ethyl acetate, to yield the 3-(1-osoisoindolino)-pyridine melting at 165°–166°.

The mixture of 3.6 g thereof, 3.6 g of 10% palladium on charcoal and 75 ml of glacial acetic acid is hydrogenated at about 65° and 3 atm until the theoretical amount of hydrogen has been absorbed. It is cooled to room temperature, filtered and evaporated. The residue is taken up in 6N aqueous sodium hydroxide, the mixture extracted with chloroform, the extract washed with saturated aqueous sodium chloride, dried and evaporated, to yield the 3-(1-oxoisoindolino)-piperidine melting at 109°–112°.

EXAMPLE 3

In the exact analogous manner, illustrated by Example 1 the 4-(1-oxoisoindolino)-piperidinium chlorides of the formula

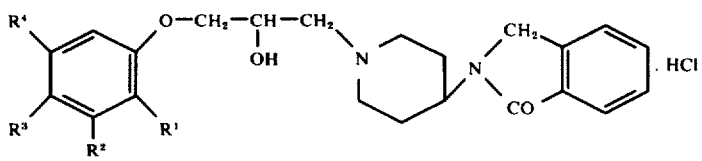

are prepared from equivalent amounts of the corresponding starting materials:

| No. | R¹ | R² | R³ | R⁴ | m.p. °C |
|---|---|---|---|---|---|
| 1 | Cl | H | H | $CH_3$ | 206–208 |
| 2 | $CH_2-CH=CH_2$ | H | H | H | 205–207 |
| 3 | $CH_2-CH=CH_2$ | $NHCOCH_3$ | H | H | 177–180 |
| 4 | cyclohexyl | H | H | H | 214–216 |
| 5 | H | H | $CH_2CONH_2$ | H | 266–270d. |
| 6 | $OCH_3$ | $OCH_3$ | H | H | 161–163 |
| 7 | $OCH_2-CH=CH_2$ | H | H | H | 185–186 |
| 8 | $OCH_2-C\equiv CH$ | H | H | H | 173–175 |
| 9 | H | H | Br | H | 253–257 |
| 10 | CN | H | H | H | 203–205 |
| 11 | H | $-(CH_2)_3-$ | | H | 270–272 |

EXAMPLE 4

To the solution of 3.96 of g of 1-[3-(o-methoxyphenoxy)-2-hydroxypropyl]-4-(1-oxoisoindolino)-piperidine (prepared from the hydrochloride of Example 1 and 2N aqueous sodium hydroxide, extracting the mixture with ethyl acetate and evaporating the dryed extract) and 2 ml of pyridine in 50 ml of methylene chloride, 1.32 g of pivaloyl chloride in 10 ml of methylene chloride are added dropwise during 20 minutes, while stirring and cooling with ice. Stirring is continued for 48 hours at room temperature, 48 hours while refluxing and again 48 hours at room temperature. The mixture is washed with cold 10% aqueous sodium carbonate and water, dried, filtered and evaporated. The residue is dissolved in 20 ml of ethanol, the solution acidified with saturated hydrogen chloride in ethyl acetate and the precipitate formed collected. It is dissolved in 50 ml of hot ethanol, 50 ml of ethyl acetate are added, the mixture cooled with ice and the precipitate formed collected, to yield the 1-[3-(o-methoxyphenoxy)-2-pivoloyloxypropyl)-4-(1-oxoisoindolino)-piperidine hydrochloride melting at 206°–212°.

EXAMPLE 5

Preparation of 10,000 tablets each containing 25.0 mg of the active ingredient:

FORMULA

| Formula: | |
|---|---|
| 1-[3-(o-methoxyphenoxy)-2-hydroxypropyl]-4-(1-oxoisoindolino)-piperidine hydrochloride | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

PROCEDURE

All the powders are passed through a screen with openings of 0.6 mm. Then the drug substance, lactose, talcum, magnesium stearate and half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 50 mg of the active ingredient:

FORMULA

| Formula: | |
|---|---|
| 1-[3-(o-cyanophenoxy)-2-hydroxypropyl]-3-(1-oxoisoindolino)-piperidine cyclamate | 500.0 g |
| Lactose | 2,350.0 g |
| Talcum powder | 150.0 g |

PROCEDURE

All the powders are passed through a screen with openings of 0.6 mm. Then the drug substance is placed in a suitable mixer and mixed first with the talcum, then with the lactose until homogenous. No. 2 capsules are filled with 300 mg, using a capsule filling machine.

I claim:

1. A 1-(3-aryloxy-2-hydroxypropyl)-3- or 4-(1-oxoisoindolino)-piperidine corresponding to the formula

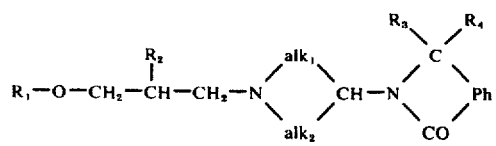

wherein $R_1$ is phenyl or phenyl substituted by one or two members selected from alkyl, alkenyl, alkinyl, 5 to 7 ring-membered cycloalkyl, carbamoylalkyl, alkoxy, alkenyloxy, alkinyloxy, halogeno, alkanoylamino, cyano, wherein said open-chain groups have up to 4 carbon atoms, $alk_1$ and $alk_2$ independently of one another are alkylene with up to 4 carbon atoms separating the adjacent nitrogen atom and methine group by either 2 carbon atoms, or alk₁ is such alkylidene and alk₂ is such alkylene separating said adjacent moieties by 3 carbon atoms, R₂ is hydroxy or alkanoyloxy with up to 4 carbon atoms, R₃ is hydrogen or alkyl with up to 4 carbon atoms, R₄ is hydrogen, and Ph is o-phenylene, or o-phenylene substituted as R₁, or a therapeutically useful acid addition salt thereof.

2. A compound as claimed in claim 1 and corresponding to the formula

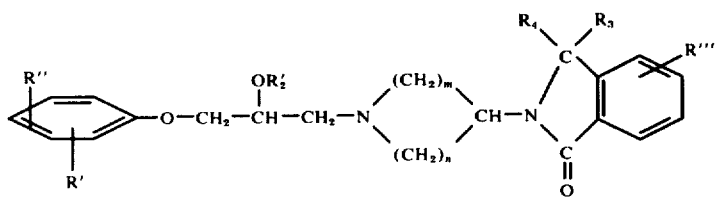

wherein m is 1 or 2, n is 2 or 3 and (m + n)is 4, R' is hydrogen, lower alkyl, lower alkenyl, lower alkinyl, 5 to 7 ring-membered cycloalkyl, carbamoyl-lower alkyl, lower alkoxy, lower alkenyloxy, lower alkinyloxy, halogeno or cyano, each of R" and R'" is hydrogen, lower alkyl, lower alkoxy, halogeno or lower alkanoylamino, R₂' is hydrogen or lower alkanoyl, wherein "lower" defines said radicals with up to 4 carbon atoms, each of R₃ and R₄ is hydrogen, or their therapeutically useful acid addition salts.

3. A compound as claimed in claim 2, in which formula said R' is in one of the ortho-positions, said R'" in one of the meta-positions or the para-position and said R'" is meta to carbonyl and para to methylene, or a therapeutically useful acid addition salt thereof.

4. A compound as claimed in claim 2, in which formula m is 1 or 2, n is 2 or 3 and (m + n) is 4, R' is methyl, allyl,cyclohexyl, carbamoylmethyl, methoxy, allyloxy, propargyloxy, chloro, bromo or cyano, R" and R'" is hydrogen, methyl, methoxy or acetylamino, R₂' is hydrogen, acetyl, propionyl or pivaloyl, and each of R₃ and R₄ is hydrogen, or their therapeutically useful acid addition salts.

5. A compound as claimed in claim 2, in which formula m is 1 or 2, n is 2 or 3 and (m + n) is 4, R' is o-methyl, o-allyl, o-cyclohexyl, p-carbamoylmethyl, o-methoxy, o-allyloxy, o-propargyloxy, o- or p-chloro, -bromo or o-cyano, R" is hydrogen, m-methyl, m-methoxy or m-acetylamino, R₂' is hydrogen, acetyl, propionyl or pivaloyl, and each of R'", R₃ and R₄ is hydrogen, or their therapeutically useful acid addition salts.

6. A compound as claimed in claim 2 and being the 1-[3-(o-methoxy- phenoxy)-2-hydroxypropyl]-4-(1-oxo-isoindolino)-piperidine or a therapeutically useful acid addition salt thereof.

7. A compound as claimed in claim 2 and being the 1-[3-(o-cyanophenoxy)-2-hydroxypropyl]-4-(1-oxo-isoindolino)-piperidine or a therapeutically useful acid addition salt thereof.

8. A hypotensive and anti-arrhythmic pharmaceutical composition comprising a hypotensively or anti-arrhythmically effective amount of the compounds claimed in claim 1, together with a pharmaceutical excipient.

* * * * *